United States Patent
Karimi et al.

(10) Patent No.: US 9,915,031 B2
(45) Date of Patent: Mar. 13, 2018

(54) PRODUCING ANTIMICROBIAL PAPER

(71) Applicants: Javad Karimi, Mashhad (IR); Saman Vahdat, Mashhad (IR); Javad Sadkharvi, Tehran (IR)

(72) Inventors: Javad Karimi, Mashhad (IR); Saman Vahdat, Mashhad (IR); Javad Sadkharvi, Tehran (IR)

(*) Notice: Subject to any disclaimer, the term of this patent is extended or adjusted under 35 U.S.C. 154(b) by 72 days.

(21) Appl. No.: 14/922,816

(22) Filed: Oct. 26, 2015

(65) Prior Publication Data
US 2016/0040363 A1 Feb. 11, 2016

Related U.S. Application Data

(60) Provisional application No. 62/068,686, filed on Oct. 26, 2014.

(51) Int. Cl.
| | |
|---|---|
| D21H 21/36 | (2006.01) |
| A01N 59/16 | (2006.01) |
| A01N 59/20 | (2006.01) |
| D21F 5/14 | (2006.01) |
| A01N 25/04 | (2006.01) |

(52) U.S. Cl.
CPC ............ D21H 21/36 (2013.01); A01N 25/04 (2013.01)

(58) Field of Classification Search
USPC ............ 162/158, 175, 176, 160, 161, 181.1, 162/181.4–181.5, 183, 185
See application file for complete search history.

(56) References Cited

U.S. PATENT DOCUMENTS

| | | | |
|---|---|---|---|
| 6,551,457 B2* | 4/2003 | Westman | D21H 23/28 162/158 |
| 2014/0176941 A1* | 6/2014 | Romero Fanego | G01N 21/65 356/301 |
| 2014/0302336 A1* | 10/2014 | Heiskanen | C08K 3/34 428/535 |

OTHER PUBLICATIONS

Definition of "bower", Merriam-Webster Dictionary, [online], retrieved from the Internet, [retrieved Mar. 2, 2017], <URL:https://www.merriam-webster.com/dictionary/bower>.*
Shan Lin, Preparation and Characterization of Chitosan/Cellulose Blend Film Using ZnCL2x3H2O as a Solvent, BioResrouces 7(4), 5488-5499 (2012).
Vipul S. Chauhan, Use of Nanotechnology for High Performance Cellulosic and Papermaking Products, Cellulose Chem. Technol., 46 (5-6), 389-400 (2012).
Majeti N.V. Ravi Kumar, A review of chitin and chitosan applications, Reactive & Functional Polymers 46 (2000) 1-27.
Jun Hosokawa, Biodegradable Film Derived from Chitosan and Homogenized Cellulose, Ind. Eng. Chem. Res. 1990, 29, 800-805.
(Continued)

*Primary Examiner* — Dennis Cordray
(74) *Attorney, Agent, or Firm* — NovoTechIP International PLLC

(57) ABSTRACT

A method for producing antimicrobial paper pulp is provided. The method includes steps of obtaining paper pulp, reducing water content and temperature of the paper pulp, and refining the paper pulp having reduced water content and temperature to improve properties of the paper pulp. The refining may be performed using a refiner with rotating and stationary cutters. The nanocomposite suspension may be added to the refined paper pulp to produce antimicrobial paper pulp. The antimicrobial paper pulp may be drained and pressed to produce paper by applying oil to reduce moisture content of the paper. The paper may be dried without using vapor.

16 Claims, 2 Drawing Sheets

(56) References Cited

OTHER PUBLICATIONS

Danuta Ciechańska, Multifunctional Bacterial Cellulose/Chitosan Composite Materials for Medical Applications, Fibres & Textiles in Eastern Europe Oct. / Dec. 2004, vol. 12, No. 4 (48).
Pranee Lertsutthiwong, Influence of chitosan characteristics on the properties of biopolymeric chitosan-montmorillonite, Progress in Natural Science: Materials International 2012;22(5):502-508.
Ming Kong, Antimicrobial properties of chitosan and mode of action: A state of the art review, International Journal of Food Microbiology 144 (2010) 51-63.
Marcin H. Struszczyk, Chitin and Chitosan, Polimery 2002,47, nr 6 396-402.
Inmaculada Aranaz, Functional Characterization of Chitin and Chitosan, Current Chemical Biology, 2009, 3, 203-230.
Visakh. P. M, Elastomeric Nanocomposites: Potential of Chitin and Cellulose Anostructures As Reinforcing Phase, 1-7 , No Date.

\* cited by examiner

PRODUCING ANTIMICROBIAL PAPER

CROSS REFERENCE TO RELATED APPLICATION

This application claims the benefit of priority to a provisional application filed at the United States Patent and Trademark Office having Ser. No. 62/068,686, filed on Oct. 26, 2014, the entire content of which is incorporated herein by reference.

TECHNICAL FIELD

The present disclosure relates generally to a method for producing antimicrobial paper.

BACKGROUND

Nanotechnological advances such as, for example, using nanofiber, nanofillers, nanocomposites and nanoscale chemicals in paper pulp production have recently been reported by papermaking industries. The recent interest in nanoscale range (e.g., material with nanoscale particle sizes) is due to the fact that advancement in technology can provide enhanced properties to nanoscale materials, as compared to the same material with larger particle sizes.

Various technologies have been developed for improving application and properties of paper and paper pulp. However, commercialized methods for producing such kind of technologically improved paper at a large scale is still missing.

Current pulp and paper mills can improve paper properties such as, for example, tensile strength and absorbance capacity. Nanotechnology methods can be useful for achieving this goal, effectively. However, since nanotechnology methods typically use non-biodegradable material, the produced paper may be harmful to the environment and natural ecosystems. Hence, there is a need for a method of producing paper that can reduce harmfulness to the environment and natural ecosystems.

SUMMARY

In one general aspect, the instant application describes a method for producing antimicrobial paper pulp. The method includes steps of obtaining paper pulp; reducing water content and temperature of the paper pulp; refining the paper pulp having reduced water content and temperature to improve properties of the paper pulp, wherein the refining is performed using a refiner with rotating and stationary cutters; adding nanocomposite suspension to the refined paper pulp to produce antimicrobial paper pulp; draining the antimicrobial paper pulp; pressing the drained antimicrobial paper pulp to produce paper by applying oil to reduce moisture content of the paper; and drying the paper without using vapor.

The above general aspect may include one or more of the following features. The water content and the temperature of the paper pulp may be reduced using a sediment pond. The draining may be performed by using blower and vacuum pump. A papermaking machine may perform the above-described method. The draining may be performed in a wire section of the papermaking machine. The antimicrobial paper pulp may have chemo-physical properties including antibacterial, antifungal, antiviral, resistance to tensile and tear, high absorbance capacity, and well drainage. The refining may cause fibers within the paper pulp to be cut or fibrillated. The nanocomposite suspension may include nano chitosan, nano cellulose, nano titanium dioxide, nano tin oxide, nano zinc oxide, nano copper oxide, nano bentonite, or a combination thereof. Adding the nanocomposite suspension to the paper pulp may include injecting the nanocomposite suspension into the paper pulp in a dark place to limit photo catalyst activity of nano titanium dioxide, nano tin oxide, nano copper oxide, and nano zinc oxide.

The amount of nano chitosan as an antibacterial agent mixed with the paper pulp may be between 0.001% and 5% of a total mass of the paper pulp. The amount of nano cellulose as an antibacterial agent mixed with the paper pulp may be between 0.001% and 5% of a total mass of the paper pulp. The amount of nano titanium dioxide and nano zinc oxide as photocatalytic agents mixed with the paper pulp may be between 0.001% and 2% of a total mass of the paper pulp. The amount of nano tin oxide, nano copper oxide and nano zinc oxide as antimicrobial agents mixed with the paper pulp may be between 0.001% and 4% of a total mass of the paper pulp. The amount of nano bentonite as a softening agent mixed with the paper pulp may be between 0.001% and 5% of a total mass of the paper pulp.

The nanocomposite suspension may include one or more thermal resistant antibiotics, such as penicillin, amoxicillin, cephalexin, erythromycin, clarithromycin, biaxin, cipro, Floxin, proloprim, garamycin, tobrex, or a combination thereof. The amount of the thermal resistant antibiotic or the combination mixed with the paper pulp may be between 0.001% and 1% of a total mass of the paper pulp.

The nanocomposite suspension may include one or more fungus with antimicrobial activities as antibacterial agents, the one or more fungus including *Colletotrichum* sp., *Phomopsis* isolate, *Periconia* sp., OBW-15, *Guignardia* sp. IFBE028, *Rhizoctonia* sp. Cy064, *Aspergillus* sp. CY725, *Pichia guilliermondii*, *Xylaria* sp. *Thielavia subthermophila*, *Ampelomyces* sp., *Fusarium* sp., *Phoma* sp., *Alternaria* sp., *Chloridium* sp., or a combination thereof. The amount of the one or more fungus as antibacterial agents mixed with the paper pulp may be between 0.001% and 1% of a total mass of the paper pulp.

The nanocomposite suspension may include one or more plant species with antimicrobial activities as antibacterial agents, the one or more plants including *Cychorium intybus* L. (Asteraceae), *Salvia officinalis* L., *Melissa officinalis* L., *Clinopodium vulgare* L. (Lamiaceae), *Torilis anthriscus* L. (Gmel), *Aegopodium podagraria* L. (Apiaceae), *Cytisus nigricans* L., *Cytisus capitatus* Scop., or a combination thereof. The amount of the one or more fungus as antibacterial agents mixed with the paper pulp may be between 0.001% and 1% of a total mass of the paper pulp. The total amount of the nanocomposite suspension may be between 10% and 25% of a total mass of the paper pulp.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

Figure 1:
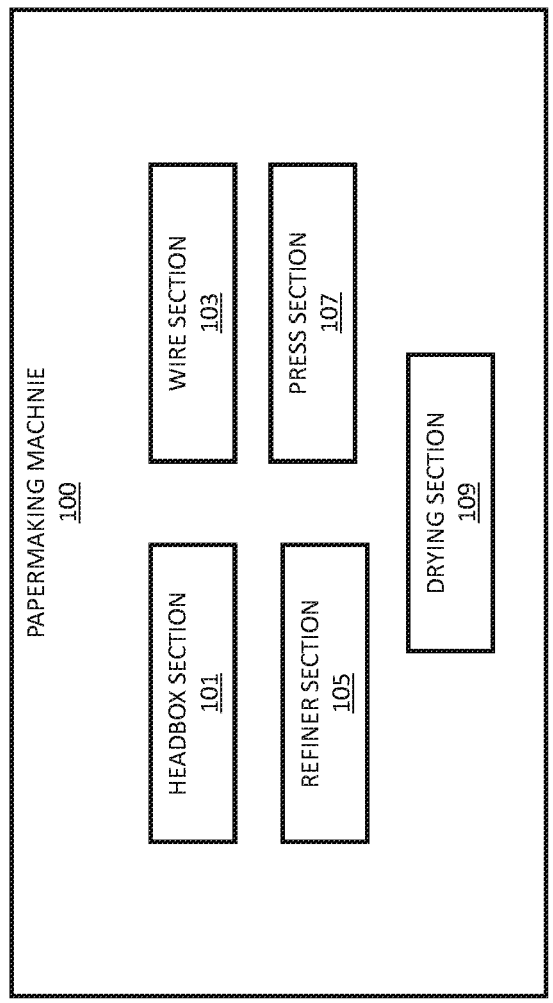
FIG. 1 illustrates a diagram of a papermaking machine and the components thereof, according to one implementation.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Cellulose is an organic compound and a biopolymer that can be found in abundance in nature and has been used for producing biodegradable paper. However lack of antimicrobial properties in cellulose based paper pulp may limit utilization of such paper pulp in hygienic paper products. On the other hand, chitosan is a linear polysaccharide composed of randomly distributed β-(1-4)-linked D-glucosamine (deacetylated unit) and N-acetyl-D-glucosamine (acetylated unit). Extended research on chitosan characteristics show antibacterial and antifungal properties of this biopolymers. Several studies have been performed to improve antimicrobials activity of cellulose based material by mixing chitosan powder in cellulose solution. The blend film of cellulose and chitosan can have partial antimicrobial properties, however the final product can be comparatively brittle. On the other hand, chitosan components in the mixture can be tremendously unstable, that is one of the major limitations in chitosan application.

Research suggest that adding specific amount of glycerol to the blend film may reduce roughness of the final product. However, it is noted that tensile strength of a composite film containing glycerol is typically much lower than the composite without glycerol. In other words, results show that glycerol may prevent bonding and complexing of cellulose and chitosan.

The polysaccharide-based membranes of chitosan and cellulose blends have been produced by using trifluoroacetic acid as a solvent. However, the chains of both biopolymers can be significantly de-polymerized and deacetylation of chitosan can also change during the process of regeneration.

The structure and properties of chitosan/bacterial cellulose film can be modified and produced in culture medium of *Acetobacter xylinum*. Biological pre-treatments such as, for example, preparing medium culture, selecting appropriate micro-organism strain, detecting different growth phase, and extracting the cellulose/chitosan material from the medium, can be expensive and may take a long time. However, the resulting product may not show significant effect on some of the properties of the films such as, for example, water vapor transmission rates, average crystallinity index, and antimicrobial capability. Meanwhile, some researchers prepared a blend film by dissolving cellulose and chitosan in N-methylmorpholine-N-oxide (NMMO) as co-solvent. Experiment performed using scanning electron microscope (SEM) indicate that when the chitosan content in the blend increases up to 3%, the surface structure of the compound becomes smoother.

Moreover, the blend film containing 5% (w/w) chitosan, may become coarse again which can be due to phase separation. In addition, environmentally friendly bio-composites can be successfully prepared by dissolving chitosan and cellulose in a NaOH/thiourea solvent. The operation conditions used in this solution system can be very harsh. As an example, the solution temperature should be kept at −12° C. during the dissolving process. Afterwards, some research has been done to manufacture an antibacterial filter-paper capable of trapping and neutralizing pathogenic microorganism using wood fiber. To produce this antibacterial paper, chitosan and nanosilver can be capped with polyacrylic acid and deposited on cellulose fibers. However, since FDA regulations prevent application of nanosilver in medical and hygienic products, nanosilver needs to be replaced by other material.

Ionic liquids such as, for example, 1,3-dimethylimidazolium chloride (DMImCl), have been used to produce stable chitosan/cellulose blend films. Although the resulted membranes have good performance, ionic liquids are expensive and not easy to recover.

The disclosed method for producing antibacterial paper pulp includes mixing antibacterial agents in scale of nanoparticles with the paper pulp to improve properties of the paper pulp such as bonding, tensile strength, antibacterial property, surface to volume ratio and absorbance capacity. The disclosed paper pulp can be upgraded from laboratory to industrial scale. In addition, no specific common solvent such as ionic solvent or aqueous salt solution, which impose extra expenses, are used. Furthermore, in the disclosed paper pulp producing method, some antibacterial agents such as chitin and chitosan material can be employed directly, while in other researches typically chitosan salts are used to improve antibacterial property. The bacterial growth rate maybe substantially decreased below the permissible threshold limit. It is noted that most of the prior art described herein may lead to limited production of antibacterial paper pulp in laboratorial scale, while the great advantages of present disclosure is its capability to be economically produced in large industrial scale.

The instant application relates to a method for producing paper pulp with chemo physical properties such as antibacterial, antifungal and antiviral properties, resistance to tensile and tear, high absorbance capacity, and well-draining property. The present disclosure provides a method for papermaking process for improving the above mentioned properties of paper pulp by employing nanocomposite suspension. The method includes obtaining paper pulp and reducing water content and temperature of the paper pulp, for example, by using a sediment pond. Subsequent to the sedimentation, nanocomposite suspension can be added to the paper pulp having reduced water content and temperature to produce antimicrobial paper pulp. The antimicrobial paper pulp can then be drained and pressed to produce paper by applying oil to reduce moisture content of the paper. The paper can then be dried without using vapor.

Typically, various processes can be used to convert logs to wood pulp. The processes include mechanical and chemical paper pulp production. In the case of mechanical paper pulp production, wood can be processed into fiber form by grinding against a quickly rotating stone under addition of water. The paper pulp can be filtered to remove foreign objects. The yield of this pulp amounts to approximately 95 percent. The produced paper pulp is called wood pulp or mechanical pulp (MP). The disadvantage of this type of pulp is that the fiber can be strongly damaged during the process and that there are various types of impurities in the pulp mass. Mechanical wood pulp may yield a high opacity, but it may not be a strong composite. It has a yellowish color and low light resistance.

For chemical production of wood pulp, pure fiber can be set free, which means that the lignin, a type of complex organic polymer in wood, has to be removed. To achieve this goal, the wood chips can be cooked in a chemical solution (e.g. sulphate and sulphite pulp). The yield of chemical pulping amounts to approximately 50%. The fibers in the resulting paper pulp can be clean and undamaged. The wood pulp produced by this process is called wood free.

Figure 2:
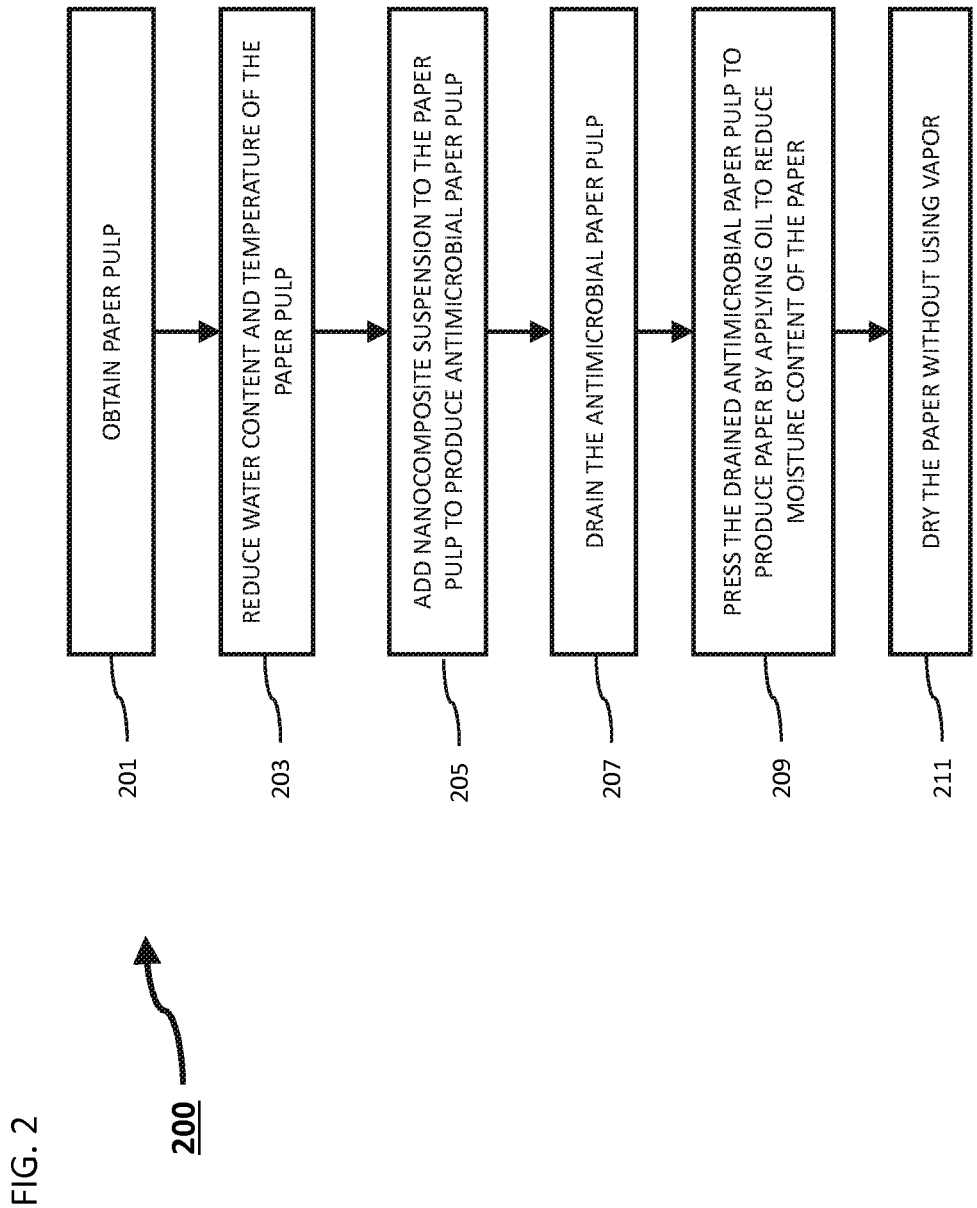
FIG. 2 illustrates an example of a process of producing antimicrobial paper, according to one implementation.

FIG. 1 illustrates a diagram of a papermaking machine and the components thereof, according to an exemplary implementation, and FIG. 2 illustrates a process producing antimicrobial paper pulp, according to an implementation. The disclosed process 200 of FIG. 2, for producing antimicrobial paper by a papermaking machine 100 of FIG. 1 is discussed herein with reference to FIGS. 1 and 2.

The process 200 begins with obtaining a paper pulp at block 201. The paper pulp may be obtained by mechanical or chemical pulping methods discussed above. The obtained paper pulp may contain a large amount of water and also can be relatively warm. At block 203, the water content and temperature of the paper pulp can be reduced, for example by the headbox section 101 of the papermaking machine 100. This may be done prior to adding the nanocomposite suspension to the paper pulp at block 205. For example, the paper pulp can be settled in mixing ponds, for example, sediment ponds (not shown) such that the moisture and temperature level of the paper pulp is reduced as desired, for example to below 30° C. (Centigrade). Parameters such as moisture and temperature of the paper pulp can be effectively adjusted by providing adequate turbulence and aeration inside the agitated sediment ponds.

The output paper pulp of the sediment ponds with controlled moisture and temperature can be injected with the nanocomposite suspension at step 205 of the process of FIG. 2. The nanocomposite suspension including nano adsorbent (e.g., nano bentonite) and nano photo catalytic particles (e.g., nano titanium dioxide (TiO2) and nano zinc oxide) can be added to the paper pulp in headbox section 101 of the papermaking machine 100. The function of the headbox section 101 may be to distribute a continuous flow of wet pulp at constant velocities. The additive nano composite suspension may include nano clay to preserve water content of produced paper pulp, such that drying of the pulp during the papermaking process can be prevented. As a result, the final product may have an excess amount of water. On the other hand, the photo catalyst activation of nano titanium dioxide (TiO2) may depend on the paper pulp temperature. High temperature of output pulp from chemical pulping may cause antibacterial properties to be released and the nano titanium dioxide particles may be deactivated. Thus, it may be important to control moisture content and temperature of the paper pulp prior to mixing the nanocomposite suspension as done in block 203.

It is noted that injection of nanocomposite suspension may occur in a dark place to limit photo catalyst activity of nano titanium dioxide, nano tin oxide, nano copper oxide, and nano zinc oxide. Prior to mixing the nanocomposite suspension additives with the paper pulp, the paper pulp can be refined, for example, in a refiner section 105 of the papermaking machine 100. The refining process can improve properties of the paper pulp. The refiner section 105 can be a refining aggregate with rotating and stationary cutters, or the so-called rotors and stators. Variable positioning of the rotors and stators in relation to each other can determine whether fibers within the paper pulp are being cut (free stock refining) or fibrillated (wet refining).

Traditionally, the papermaking process material include water, fillers, sizing substances, dyes and additives. Fillers serve multiple purposes such as, for example, making the paper more opaque, brighter in shade as well as softer and more flexible based on the requirement. The total percentage of fillers used can be as high as 30% of the stock.

The present disclosure includes using nanocomposite suspension in addition to using the traditionally used additive materials. The nanocomposite suspension may include, nano chitosan, nano cellulose, nano clay (e.g. bentonite), nano zinc oxide, nano tin oxide, and nano TiO2 in the paper pulp. The nanocomposite suspension material can improve properties of paper products. Since the mentioned particles are in nano scale, their unique properties can be reinforced in the paper product. By adding nanocomposite suspension into paper pulp (shown at block 205 of FIG. 2), important parameters such as, for example, tensile strength and adsorption capacity of the paper can be enhanced and also unique antimicrobial properties can be created, for example, due to presence of nano chitosan and nano TiO2. The total percentage of mentioned nanocomposite suspension used can be in range of 10 to 25 percent of the stock.

Nano chitosan, nano copper oxide, nano zinc oxide and tin oxide present in the nanocomposite suspension can enhance antibacterial activity of paper pulp. However, poor stability of chitosan in nanocomposite suspension can be a limiting factor in its utilization. To solve the issue, chitosan salts can be used to ameliorate the instability of chitosan in the nanocomposite suspension. The main drawback of employing these kinds of chitosan salts is their high expense. Thus the high price of chitosan salts prevents using such material in the industrial scale. In one implementation of the present disclosure, nano cellulose can be used to strengthen stability of chitosan in the nanocomposite suspension. In other word, chitosan film is frail, and nano cellulose resolves this problems. Cellulose is structurally similar to chitosan and therefore cellulose can create secured bind inside the nanocomposite suspensions. Preferably using nano cellulose may reduce the cost of paper pulp manufacturing compared to utilizing nano chitosan salts and it makes the final product more affordable in large scale production.

The present disclosure includes using metal salts and their oxides for paper pulp production. The produced paper pulp can be used for production of various paper products such as, for example, tissue paper, various types of sanitary pads, baby and senior diapers. Metal salts, either in free state or in compounds, are toxic to microbes at very low concentrations. The salts can kill microbes by binding to intracellular proteins and inactivating them. Preparation of nano-sized metals and metal oxides, mainly silver (Ag), titanium dioxide (TiO2), zinc and tin oxide (ZnO) and copper II oxide (CuO) has enabled the development of a new generation of biocides.

Nano titanium dioxide in the nanocomposite raises antimicrobial activity during the paper pulp production process. Titanium dioxide is a type of material with a high photo catalytic activity which guaranteed protection of paper pulp from bacterium attacked during the production procedure. The photo catalytic activity generally starts by receiving energy. The energy can be provided by heating and/or lighting the paper pulp during production procedure. In order to limit photo catalytic activity of nano dioxide titanium, nanocomposite suspension can be injected into the paper pulp in a dark environment.

In one implementation, the amount of nano chitosan as an antibacterial agent mixed with the paper pulp can be between 0.001% and 5% of the total mass of the paper pulp (e.g., a mass fraction of the total mass). The amount of nano cellulose as an antibacterial agent mixed with the paper pulp can be between 0.001% and 5% of the total mass of the paper pulp. The amount of nano titanium dioxide and nano zinc oxide as photocatalytic agents mixed with the paper pulp can be between 0.001% and 2% of the total mass of the paper pulp. The amount of nano tin oxide, nano copper oxide and nano zinc oxide as antimicrobial agents mixed with the paper pulp can be between 0.001% and 4% of the total mass of the paper pulp. The amount of nano bentonite as a softening agent mixed with the paper pulp can be between 0.001% and 5% of the total mass of the paper pulp.

In some exemplary implementations, the nanocomposite suspension may include one or more thermal resistant antibiotics, such as penicillin, amoxicillin, cephalexin, erythromycin, clarithromycin, biaxin, cipro, Floxin, proloprim, garamycin, tobrex, or a combination thereof. The amount of the thermal resistant antibiotic or the combination mixed with the paper pulp may be between 0.001% and 1% of a total mass of the paper pulp.

In some exemplary implementations, nano clay (e.g., bentonite) including fungus substances can be added to the nanocomposite suspension. For example, the fungus can be one or more of *Colletotrichum* sp., *Phomopsis* isolate, *Periconia* sp., OBW-15, *Guignardia* sp. IFBE028, *Rhizoctonia* sp. Cy064, *Aspergillus* sp. CY725, *Pichia guilliermondii*, *Xylaria* sp. *Thielavia subthermophila*, *Ampelomyces* sp., *Fusarium* sp., *Phoma* sp., *Alternaria* sp., and *Chloridium* sp., and the amount of the added fungus can be from 0.001% to 1% of the mass fraction of the nanocomposite suspension. In addition, nano particles of selected plant species such as, for example, *Cychorium intybus* L. (Asteraceae), *Salvia officinalis* L., *Melissa officinalis* L., *Clinopodium vulgare* L. (Lamiaceae), *Torilis anthriscus* L. (Gmel), *Aegopodium podagraria* L. (Apiaceae), *Cytisus nigricans* L., *Cytisus capitatus* Scop., can also be added to the nanocomposite suspension with same amount of 0.001% to 1% of the mass fraction. The total amount of the nanocomposite suspension can be between 10% and 25% of the total mass of the paper pulp.

The nano clay can accomplish various functions in the nano composite suspension. For example, the nano clay can improve the moisture content of the paper pulp as a reinforced absorbent. In addition, the nano clay can increase tensile strength of the paper pulp. Increasing moisture content of paper pulp results in softness and smoothness of final product. Chitosan nano particles can cause severe adhesion properties in the paper pulp due to high viscosity of the chitosan. Therefore, chitosan may cause the paper pulp to become brittle. Accordingly, in order to resolve above issue, the present disclosure includes using nano clay which can make the product softer by increasing the pulp moisture content.

At block 207 of FIG. 2, the paper pulp can be drained, for example, by squeezing, in the headbox section 101 of the papermaking machine 100, a mixture of the processed paper pulp (obtained from pervious step 205) and water. Subsequent to squeezing, the output mixture can be uniformly spread onto mesh plates with specified thickness (e.g., up to 18 millimeters) to drain (shown as block 207 of FIG. 2). Principally, the exit velocity of paper pulp from the headbox section 101 onto a paper forming wire section 103 can be equal to the speed of a wire on which the paper is formed. Furthermore to avoid harmful flock formation, adequate turbulence can be generated in outlet of the headbox section 101.

In the wire section 103, the paper pulp can move on the wire and a layer of fiber can be formed on the wire. While the fiber layer is forming, excess water can drain away at bottom of the mesh grid plate. As previously discussed, nano adsorbent particles in the nanocomposite suspension can largely reduce the amount of water drainage in wire section 103. In order to enhance water drainage, the length of the wire section 103 can be increased 1.5 folds which can enhance production time. Since increased production timeframe is not economically desirable in industrial scale, the present disclosure includes using equipment such as blowers and vacuum pumps (not shown) to improve the water drainage in wire section 103. Thus in this way, both side of paper pulp can be drained simultaneously by mounting blower and vacuum pumps at top and bottom of the wire section 103 respectively.

At block 209 of FIG. 2, upon formation of paper sheets, the paper sheets can be further drained and compressed in a press section 107. In the press section 107 of the papermaking machine 100 of FIG. 1, paper web can run between a series of rolls which exert specific set amounts of pressure on the paper. The water pressed out of the paper can be collected and recycled. In recent years, shoe presses have been developed to increase the efficiency of the traditional roll presses. For example, in some modern press units, the major roll can be replaced by a hydraulically pressed shoe.

The present disclosure provided a method for improving pressuring and water drainage from paper products. In the disclosed method, the press section 107 may include several double glazed cylinders which use oil to fill wall spaces, for example by an approximate thickness of 40 centimeters. Due to the high thermal capacity of oil, heating energy cab be saved. As a result, paper production cost can be reduced while high quality of the product can be achieved.

The paper leaving the press section 107 of the papermaking machine, can have a dry content of up to 50-55%. At this stage, as shown in block 211 of FIG. 2, the remaining water can be removed by vaporization in a drying section 109 of the paper making machine 100. The most common type of paper drying is contact drying on cylinders heated with vapor (not shown). In one implementation, the heat energy can be transferred from outside walls of the drying cylinders to the paper surface by direct contact. The dryer section 109 may consist of a succession of drying cylinders and the paper web can be transported over and between the cylinders. In the disclosed method, due to employing nano clay (as reinforce absorbent), the paper humidity can be retained in an optimum level, and therefore there is no need to inject excess vapor in drying section.

The papers prepared in the above described manner can have high tear resistance and absorption capacity. Moreover, the paper also has unique antibacterial properties. Thus the final paper can be useful in hygienic applications in products such as diapers, sanitary pads, towel napkins, etc.

The separation of various system components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 105 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A method for producing antimicrobial paper pulp comprising:
   obtaining paper pulp;
   reducing water content and temperature of the paper pulp;
   refining the paper pulp having reduced water content and temperature to improve properties of the paper pulp, wherein the refining is performed using a refiner with rotating and stationary cutters;
   adding nanocomposite suspension to the refined paper pulp to produce antimicrobial paper pulp;
   draining the antimicrobial paper pulp;
   pressing the drained antimicrobial paper pulp to reduce moisture content of the drained antimicrobial paper pulp and produce paper; and
   drying the paper without applying vapor to the paper.

2. The method of claim 1, wherein the water content and the temperature of the paper pulp are reduced using a sediment pond.

3. The method of claim 1, wherein the draining is performed by using a blower and a vacuum pump.

4. The method of claim 1, wherein the antimicrobial paper pulp has chemo-physical properties including antibacterial, antifungal, antiviral, resistance to tensile and tear, high absorbance capacity, and well drainage.

5. The method of claim 1, wherein the refining causes fibers within the paper pulp to be cut or fibrillated.

6. The method of claim 1, wherein the nanocomposite suspension includes nano chitosan, nano cellulose, nano titanium dioxide, nano tin oxide, nano zinc oxide, nano copper oxide, nano bentonite, or a combination thereof.

7. The method of claim 6, wherein adding the nanocomposite suspension to the paper pulp includes injecting the nanocomposite suspension into the paper pulp in a dark place to limit photo catalyst activity of nano titanium dioxide, nano tin oxide, nano copper oxide and nano zinc oxide.

8. The method of claim 6, wherein amount of nano chitosan as an antibacterial agent mixed with the paper pulp is between 0.001% and 5% of a total mass of the paper pulp.

9. The method of claim 6, wherein amount of nano cellulose as an antibacterial agent mixed with the paper pulp is between 0.001% and 5% of a total mass of the paper pulp.

10. The method of claim 6, wherein amount of nano titanium dioxide and nano zinc oxide as photocatalytic agents mixed with the paper pulp is between 0.001% and 2% of a total mass of the paper pulp.

11. The method of claim 6, wherein amount of nano tin oxide, nano copper oxide and nano zinc oxide as antimicrobial agents mixed with the paper pulp is between 0.001% and 4% of a total mass of the paper pulp.

12. The method of claim 6, wherein amount of nano bentonite as a softening agent mixed with the paper pulp is between 0.001% and 5% of a total mass of the paper pulp.

13. The method of claim 1, wherein:
   the nanocomposite suspension includes a thermal resistant antibiotic, such as penicillin, amoxicillin, cephalexin, erythromycin, clarithromycin, biaxin, cipro, Floxin, proloprim, garamycin, tobrex, or a combination thereof, and
   amount of the thermal resistant antibiotic or the combination mixed with the paper pulp is between 0.001% and 1% of a total mass of the paper pulp.

14. The method of claim 1, wherein:
   the nanocomposite suspension includes one or more fungus with antimicrobial activities as antibacterial agents, the one or more fungus including *Colletotrichum* sp., *Phomopsis* isolate, *Periconia* sp., OBW-15, *Guignardia* sp. IFBE028, *Rhizoctonia* sp. Cy064, *Aspergillus* sp. CY725, *Pichia guilliermondii*, *Xylaria* sp., *Thielavia subthermophila*, *Ampelomyces* sp., *Fusarium* sp., *Phoma* sp., *Alternaria* sp., *Chloridium* sp., or a combination thereof, and
   amount of the one or more fungus as antibacterial agents mixed with the paper pulp is between 0.001% and 1% of a total mass of the paper pulp.

15. The method of claim 1, wherein:
   the nanocomposite suspension includes one or more plant species with antimicrobial activities as antibacterial agents, the one or more plants including *Cychorium intybus* L. (Asteraceae), *Salvia officinalis* L., *Melissa officinalis* L., *Clinopodium vulgare* L. (Lamiaceae), *Torilis anthriscus* L. (Gmel), *Aegopodium podagraria*

L. (Apiaceae), *Cytisus nigricans* L., *Cytisus capitatus* Scop., or a combination thereof, and amount of the one or more fungus as antibacterial agents mixed with the paper pulp is between 0.001% and 1% of a total mass of the paper pulp.

16. The method of claim 1, wherein a total amount of the nanocomposite suspension is between 10% and 25% of a total mass of the paper pulp.

* * * * *